United States Patent [19]

Turner

[11] Patent Number: 4,860,752

[45] Date of Patent: Aug. 29, 1989

[54] INVASIVE MICROWAVE ARRAY WITH DESTRUCTIVE AND COHERENT PHASE

[75] Inventor: Paul F. Turner, North Salt Lake, Utah

[73] Assignee: BSD Medical Corporation, Salt Lake City, Utah

[21] Appl. No.: 161,456

[22] Filed: Feb. 18, 1988

[51] Int. Cl.[4] ............................................. A61N 5/02
[52] U.S. Cl. ................................. 128/422; 128/399; 128/804
[58] Field of Search ............... 128/399, 401, 422, 784, 128/786, 804, 303.12

[56] References Cited

U.S. PATENT DOCUMENTS

| 4,397,314 | 8/1983 | Vaguine | 128/399 |
| 4,448,198 | 5/1984 | Turner | 128/422 |
| 4,638,436 | 1/1987 | Badger et al. | 128/401 |

OTHER PUBLICATIONS

Control of the SAR Pattern Within an Interstitial Microwave Array Through Variation of Antenna Driving Phase, B. Stuart Trembly et al., IEEE Transactions on Microwave Theory and Techniques, vol. MTI-34, #5, 5/86.
Cancer Therapy by Hyperthermia and Radiation, J. P. C. Le Bourgeois et al., Urban & Schwarzenberg, Baltimore-Munich, 1978.

Primary Examiner—Francis J. Jaworski
Assistant Examiner—George Manuel
Attorney, Agent, or Firm—Hubbard, Thurman, Turner & Tucker

[57] ABSTRACT

The hyperthermia treatment apparatus includes an invasive microwave array of applicators with destructive and coherent phase. The desired power phase shift is obtained either by (1) insertion of pre-calibrated phase shift modules or cables, (2) adjustment to the phase of an in-line electronic phase shifter, (3) adjustment of mechanically movable phase shifters such as ferrite or sliding length coaxial line stretchers. A computer provides the proper selection of radiated power for each applicator using a look up table of pre-treatment planning software calculations, and the adjustment of power levels to that determined by the pre-treatment plan. At least one applicator is centrally located with respect to applicators located peripherally. The power and phase shift applied to the central located applicator is computed and applied such as to partially cancel the in phase (coherent) power of the peripheral applicators to substantially reduce the temperature of the centrally located hot spot and provide substantially uniform temperature in the area formed by the applicators using a minimum number of applicators.

7 Claims, 7 Drawing Sheets

■ ANTENNA LOCATIONS
□ DATA POINT LOCATIONS

| APPL# | POWER | PHASE |
|---|---|---|
| 1-6 | 3.0 W | 0° |

INITIAL ESTIMATED
TEMPERATURE PATTERN, °C
NO CENTRAL APPLICATOR

INVASIVE MICROWAVE ARRAY WITH DESTRUCTIVE AND COHERENT PHASE

This invention relates to systems for heating human or animal tissue (hyperthermia) and more particularly to an improved apparatus for improved heating local areas within such body tissue.

BACKGROUND OF THE INVENTION

As is generally known, death, or necrosis, of living tissue cells occurs at temperatures elevated above a normal cell temperature. Further, the death rate of such heated tissue is a function of both the temperature to which it is heated and the duration for which the tissue is held at such temperatures.

It is also well known that the elevation of temperatures of living tissue can be produced with electromagnetic energy at frequencies greater than about 10 KHz.

It has been reported that some types of malignant cells may be necrotized by heating them to a temperature which is slightly below the temperature injurious to most normal cells. In addition, some types of malignant cells may be selectively heated and necrosed by hyperthermia techniques because masses of these malignant cells typically have considerable poorer blood flow and thus poorer heat dissipation properties than does the surrounding normal tissue. As a result, when normal tissue containing such malignant masses is heated by EMR (electromagnetic radiation), the resultant temperature of the malignant mass may be substantially above that of surrounding healthy tissue.

It has been determined that most malignant cells have a relatively limited temperature range in which hyperthermia is effective in causing tumor necrosis. Above a threshold temperature of about 41.5 degrees Celsius, substantial thermal damage occurs even in those types of malignancies which have a greater sensitivity to temperature than do normal cells. In fact, at temperatures just below this threshold, growth of some types of malignancies may be stimulated. At temperatures above 45 degrees Celsius thermal damage to most normal cells occur when exposed more than 30 minutes. A discussion of hyperthermia in the treatment of cancer is contained in "Physical Hyperthermia and Cancer Therapy" by J. Gordon Short and Paul F. Turner in the "Proceeding of the IEEE", Vol. 68, No. 1, January, 1980 herein incorporated by reference.

Typically, EMR heating of body tissue is accomplished by holding an EMR radiator, or applicator, adjacent to, or against, exterior portions of a body, the EMR then penetrating and heating subsurface portions of tissue. However, significant amounts of energy are absorbed by surface or epidermic layers which may have to be cooled in order to prevent damage thereto by overheating.

The amount of penetration, or the depth of which EMR causes effective heating, is dependent upon the frequency of radiation.

For example, in accordance with an article by A. W. Guy, et al, published in proceedings of the IEEE, Vol. 63, No. 1, January, 1974 entitled "Therapeutic Application of Electromagnetic Power", the depth of penetration in the human muscle and fat at 100 MHz is 6.66 cm and 60.4 cm, respectively, while at 915 MHz the depth of penetration is only 3.04 cm and 17.7 cm, respectively.

In general, the lower the EMR frequency, the larger the applicator must be in order to effectively radiate the energy into the tissue and, as a result, applicators for radiating EMR below one gigahertz tends to be large in size and cumbersome to handle. Additionally, such applicators are not configured to selectively heat tumors of various sizes and shapes located well beneath the surface layer of the body being irradiated. Further, tumors, or other selected areas, shielded by a layer of boney tissue such as a skull, are difficult to effectively heat deeply with externally applied EMR.

Invasive EMR applicators, that is, radiators which can be inserted into body tissue to the region either within or adjacent to malignant tumors, or other localized growths, for selective heating thereof, may cause nonuniform heating or "hotspots" at or nearest the surface of such applicators because of nonuniform field distributions. Such unwanted "hot spotting" is more likely to cause serious overheating when such invasive applications are operated at higher power levels in order to heat large localized growths using a single applicator. Such growths may be many times the size of the radiating area of an invasive type applicator. Examples of invasive EMR applicators are disclosed in U.S. Pat. Nos. 4,448,198 and 4,669,475 entitled "Invasive Hyperthermia Apparatus and Method" which disclose the application of several invasive type applicators and methods of using the apparatus to effectively heat relatively large localized areas within living body tissue, without significant hot spotting at or about the applications.

The localized areas included those located well beneath surface layers of the body tissue. According to the method disclosed, the heating of these local regions within living body tissue were accomplished with a radiation source providing electromagnetic radiation to several applicators. Each of the applicators were adapted for insertion into the body tissue and for radiating EMR energy therein.

In addition to the applicators, several invasive temperature probes were disclosed for monitoring temperatures within a target growth and also the normal tissue just outside the target growth.

The improved applicators provided an applicator for insertion into body tissue for radiation of EMR and for the detection of temperature therein. This enables the system to provide radiation to the applicators in accordance with the sensed temperatures to control the heating of localized areas of body tissue. This also included a system for controlling radiation provided to localized areas of body tissue by calibrating the applicator temperature sensor to determine the portion of measured temperature resulting from the heating of the applicator.

An article by B. Stuart Trembly et al. entitled "Control of the SAR Pattern Within an Interstitial Microwave Array through Variation of Antenna Driving Phase", published in IEEE Transactions on Microwave Theory and Techniques, Vol. MTT-34, No. 5, May 1986, also demonstrated the use of peripheral applicator phase change in a continuous manner as was contained within U.S. Pat. No. 4,448,198. This continuous phase variation is shown to provide improved uniformity over the fixed phase examples of coherent arrays. Further, the region of large SAR (specific absorption rate) can be shifted within the array by changing the driving phases so as to create phase coherence at a point other than the center.

The disadvantage of the prior art references is that they contain substantial limitations to control the temperature of the region of large SAR. Clinically it is not very satisfactory to place so much heat in the central zone of an implant with much less along the margins which is a characteristic of large coherent phased arrays. Usually, there may be impaired central tumor blood flow (in necrotic zones) which would enable further central temperature elevation above the perimeter zones. Although it is possible to moderate the power to each applicator of this array, there would not be a change of this basic central heating phenomena and the clinician would be faced with a difficult decision during treatment: either central temperature would be allowed to approach 50 degrees Celsius to enable perimeter heating to 42 degrees Celsius or non-therapeutic temperatures would encompass the implant perimeter. Above about 45 degrees Celsius, healthy tissue can be damaged. To partially overcome excess heating near the antenna, more antennas had to be inserted into the patient. The ideal method is to both minimize the required number of antennas, and to maximize the uniformity.

SUMMARY OF THE INVENTION

In accordance with the present invention the heating of a central interference zone is altered by injecting an energy cancellation field to reduce the heating from the central constructive interference. This central partial destructive interference zone serves to improve heating to the periphery of the array by making the absorbed power density (or SAR) more uniform within the array and increasing perimeter heating. The selection of the relative phase of the EMR in the central region is computer determined and controlled and the amplitudes of the EMR can be determined either from the computer solution or by observing the heating indicated by the array antennas internal thermometry.

Accordingly, it is an object of the present invention to provide an apparatus for producing improved uniformity in tissue heating by creating in a central zone partially destructive interference.

Another object of the invention is to provide an apparatus for producing an acceptable heating of the central zone which increases heating to the outer perimeter of the many geometries of the malignant tissues to be treated.

A further object of the invention is to provide an apparatus whose selected relative phase for the EMR in the central region can be computed by hand or by computer to estimate the proper phase.

Still another object of the invention is to provide an apparatus having the capability for pre-treatment planning of the amplitude balance both originally and continuously thereafter.

BRIEF DESCRIPTION OF THE DRAWINGS

Other objects and features of the invention will become more readily apparent from the following detailed description when read in conjunction with the accompanying drawings.

DETAILED DESCRIPTION OF A PREFERRED EMBODIMENT

This invention includes an apparatus having an array of applicators arranged in such geometric configurations as circles, triangles, rectangles, and squares with at least one applicator centrally disposed thereto. The central applicator(s) has its phase shift varied to partially cancel what would otherwise be a central hot spot of a coherent phase array. The selection of phase (Pt) is easily estimated by multiplying the average distance in centimeters between the centrally disposed applicator(s) and each applicator of the peripheral applicators by the frequency of the microwave signals in Hz and a constant 0.0894.

The array of applicators is an invasive microwave array which uses synchronous but different relative phase to improve the heating uniformity within the implanted volume. The device provides the desired phase shift by either (1) inserting in the circuit pre-calibrated phase shift modules or cables, (2) adjustment to the phase of an in-line electronic phase shifter, or (3) adjusting mechanically movable phase shifters such as ferrite or sliding length coaxial line stretchers. Also, the proper selection of radiated power of each applicator is made using pre-treatment planning software calculations, and the adjustment of power levels to that determined by the pre-treatment plan.

The phase shift is simply determined by the phase lag introduced by, for example, a coaxial cable with relative dielectric constant (k) material between the center and outer conductor. The phase shift (P) is determined from the cable length in cm (L), the operating frequency in MHz (F) and the coaxial dielectric (K). The formula is $P = 0.012 LF(K)^{\frac{1}{2}}$, degrees lag.

The adjustment of the phase by electronic phase shifters is controlled by changing the applied dc voltage which normally alters the capacitance of an internal reflective varactor diode. Suitable phase shifters are commercially available from companies such as Wherlatone, Inc., Waveline Inc., and Adams-Russell Electronics Co.

The adjustment of the phase shift by mechanical phase shifters with ferrite is generally done by inserting ferrite between the inner and outer conductors of a transmission line. This delays the phase and normally decreases the amplitude. Changing the phase by a coaxial line stretcher is also common as a phase shifter. Both mechanical phase shifters suitable for this invention are commercially available (i.e. Microlab/FXR, Waveline Inc. and ARRA).

Thus, in operation microwave radiation is distributed to these applicators with preselected phases. These, applicators together provide substantially uniform heating of the inside area sufficient to destroy cancerous growth therein, but leaves the normal living tissue surrounding the cancerous growth unharmed. The use of the centrally located applicators maximizes the distance between opposing peripheral applicators; this minimizes the number of peripheral applicators necessary for a given treatment area. The apparatus includes a temperature measuring capability to determine the resulting heating of tissue surrounding the applicators.

Figure 1:
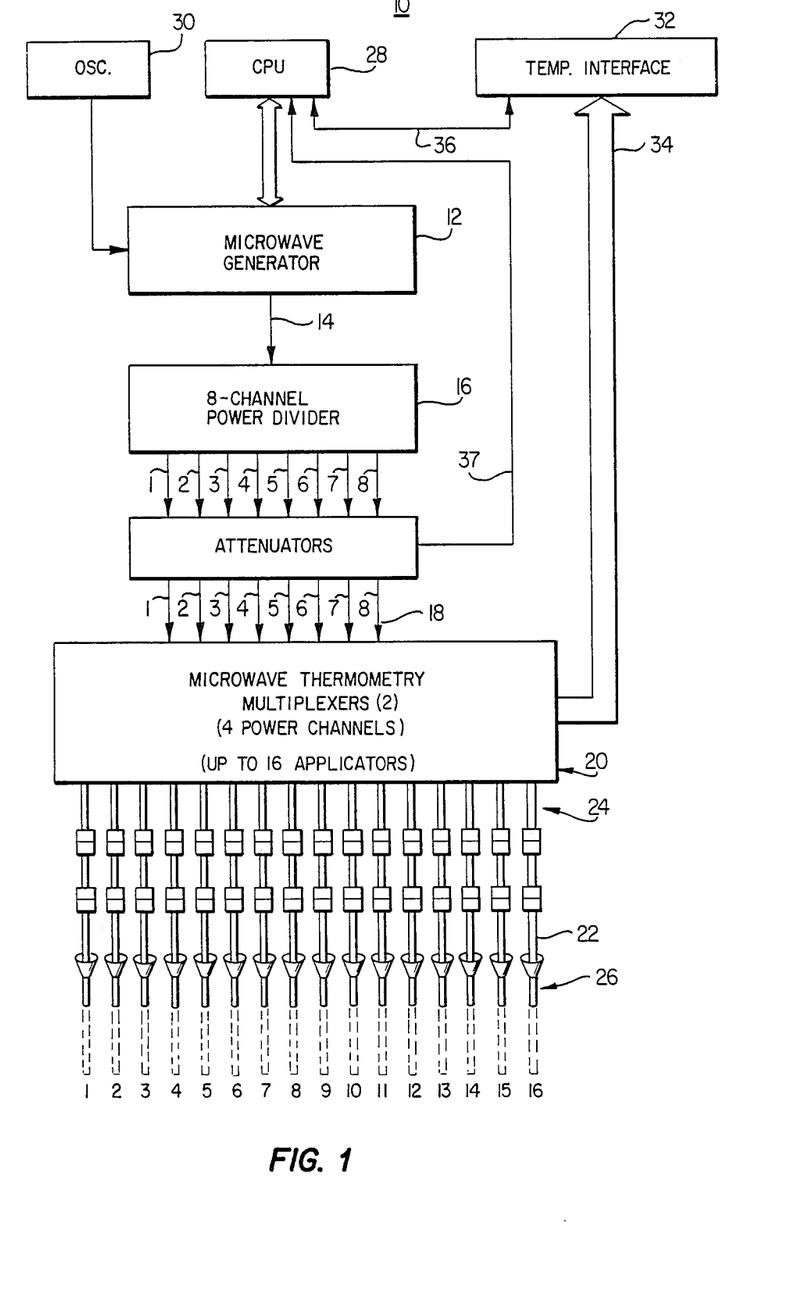
FIG. 1 is a block diagram of the electromagnetic hyperthermia apparatus.

Referring now to FIG. 1, the invasive microwave array with destructive and coherent phase apparatus 10 includes a microwave generator 12 that is connected by one or more RF power transmission lines to a power divider 16 (one or more). The power divider distributes power over, for example, 8 lines 18 to microwave thermometry multiplexer 20. Multiplexer 20, for example, consists of two identical modules. In the preferred embodiment, the microwave generator is between a 400 to 915 megahertz generator producing between 0 to 50 watts adjustable power for each channel used provided by attenuators or variable gain amplifiers 39 following the power dividers. Each multiplexer 20 is connected to up to 8 probes via RF transmission lines 24 or can contain additional power dividers to increase the number of applicators. For example, the microwave thermometry multiplexers 20 are each connected to 8 transmission lines 24 that are respectively connected to 8 applicators 22. The applicators are inserted inside catheters 26 which have been placed in the tissue to be heated.

The amount of power provided to each applicator is controlled by a central processing unit (computer) 28 as specified by the operator. The control of the generator output power may also be controlled manually. The generator contains one common oscillator 30 to provide synchronous phase to each power divider. The central processing unit 28 controls the amount of RF power distributed to each of the multiplexers 20 with control lines 37. It should be understood that the channel power gain controls may also be replaced by any means for changing power channel gain such as attenuator or regulating power distribution to the multiplexer such as switches, amplifiers, mismatched tuning sections or the like.

The applicators 22 all may include temperature sensors. The temperature sensors are also connected to the microwave thermometry multiplexers 20 through lead lines 24. The output of the temperature sensors are then connected to the temperature interface circuitry 32 via bus 34. The temperature sensor information is then provided to the central processing unit 28 via line 36. In practice, the output of the microwave thermometry multiplexer may be a single multiplexed line for all the sensors connected to the multiplexer or it may be individual discrete lines from each of the applicators to the temperature interface circuitry 32. The central processing unit 28 will be able to adjust the amount of radiated power to the applicators in accordance with the indicated temperature to treat the tissue area with a predetermined heating pattern. During treatment, the central processing unit 28 will monitor the indicated tissue temperature from the applicators and make whatever adjustments are necessary to the radiated power distributed to the applicators. If some applicators are not provided with temperature sensors the power is regulated by either another neighboring applicator sensor or non-applicator inserted temperature sensor.

Figure 2:
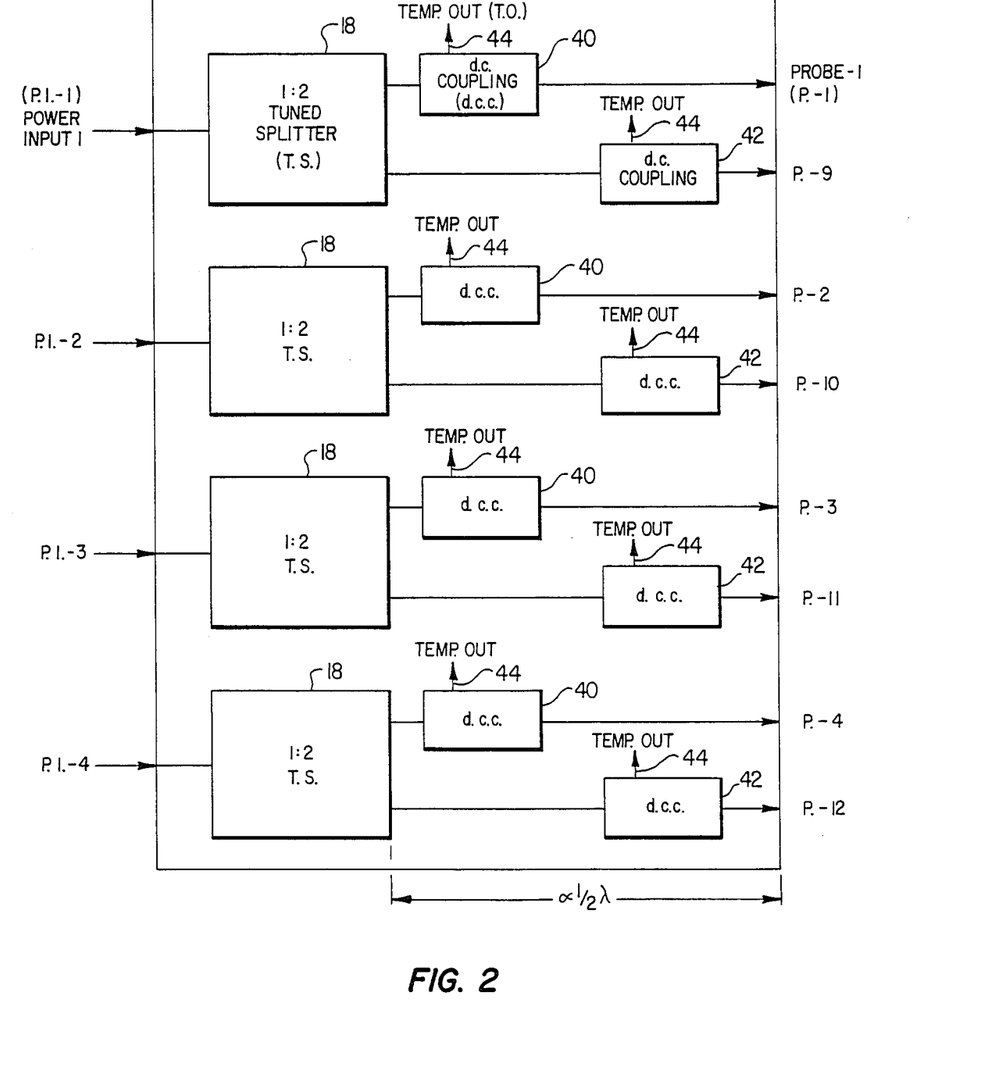
FIG. 2 is a block diagram showing one half of the microwave thermometry multiplexer system.

Referring now to FIG. 2, the microwave thermometry multiplexing system for each half shows power inputs 1-4 of input lines 18 connected to 1:2 tuned splitters 38. Each tuned splitter divides the power between dc couplers 40 and 42 and outputs temperature information to the temperature interface 32 on lines 44 of bus 34. The microwave energy is provided at a preselected phase, respectively, on probes 1 and 9, 2 and 10, 3 and 11, and 4 and 12 of probes 22 by either inserting cables or phase shifters at the outputs P1 to P12 prior to probe attachment. The other half of the full microwave thermometry multiplexer system outputs are to, respectively, probes 5 and 9, 6 and 10, 7 and 11, and 8 and 12. Thus, 8 inputs are received and 16 outputs made to the probes. An alternate method to provide phase shift is to add variable phase shifters as a part of each channel in the variable gain amplifier section 39.

It will be appreciated that the required phase shift can be made within the power divider 16, the divider cables 18, the multiplexer 20, the variable gain amplifiers 39 or the applicator cables. Also, that any number of applicators up to 16 can be used.

Those persons skilled in the art desiring more information for the system components are referred to U.S. Pat. No. 4,669,475.

It has been found that the probes 22 can be arranged peripherally around a tumor with one or more centrally located within the tumor to selectively cancel a portion of the energy received at the center of the tumor while maintaining the phase necessary to produce the desired temperature substantially uniformly throughout the tumor. The arrangement includes the minimum number of probes for the tumor area, and having a peripheral geometry that corresponds to the shape of the tumor. The probe insertion geometry between neighboring probes can be triangular, rectangular, square, or circular.

EXAMPLE

It has been important to verify and establish a level of confidence in the numerical treatment planning prior to clinical application. The pretreatment planning, does not yet include the effects of blood flow modifying the heat pattern. This parameter is not included partly because it is not known in most clinical hyperthermia. Thus, this factor would require clinicians to guess about blood flow to provide correct input. Blood flow is not generally uniform within tumor volume and changes both during hyperthermia as well as between treatments of the same patient. Also, the computation time would greatly increase to include all blood flow effects. Therefore, the current treatment planning shows the temperature pattern expected when rapidly heating a tumor equivalent phantom from 37 degrees Celsius to a maximum of 45 degrees Celsius. This is called the Thermal Equivalent SAR (specific absorption rate) pattern.

Verification of the pretreatment plan is best performed by heating of a tumor equivalent phantom.

Figure 3:
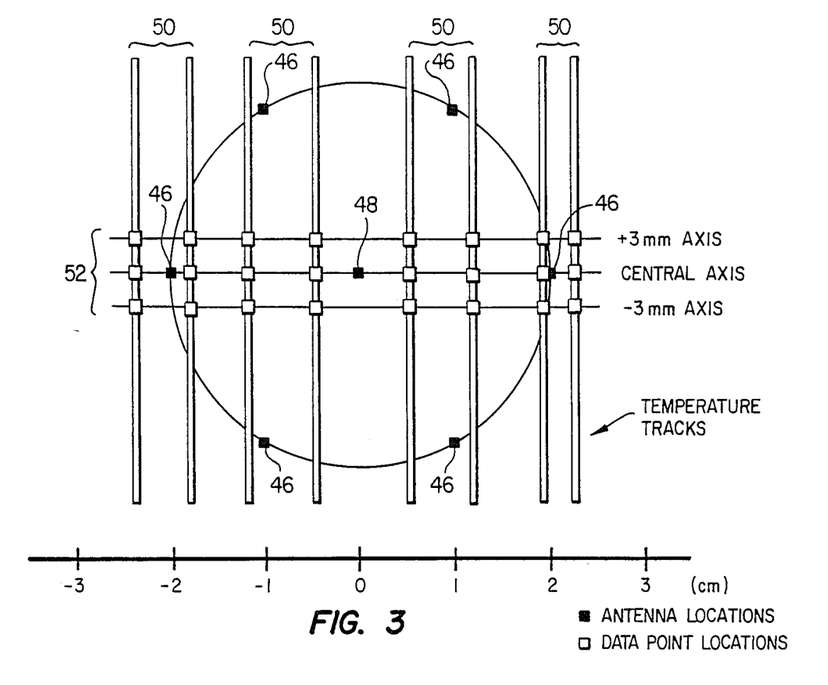
FIG. 3 is a view showing an apparatus configured with an array of six antenna catheters and a centrally located seventh antenna catheter for use with or without the centrally located antenna during heat verification testing.

To verify the correctness of the numerical model a tumor/muscle equivalent phantom was assembled with a 4 cm diameter implant in a cylindrical pattern within a 15 cm diameter phantom cylinder. FIG. 3 shows the 6 antenna catheter location along the 4 cm diameter as solid squares 46. An additional solid square 48 in the center shows another antenna catheter which was utilized during some of the heat verification testing.

Other 16 gauge plastic catheters were placed perpendicular to the antenna catheters and are shown (FIG. 3) as long vertical rectangles 50. The open squares 52 along these catheter tracks show the locations at which temperatures were measured during 60 second heat-up tests. The 3 horizontal lines shown (+3 mm, central, and −3 mm axis) represent the plotted display axes used in displaying the test results.

RESULTS

Figure 4:
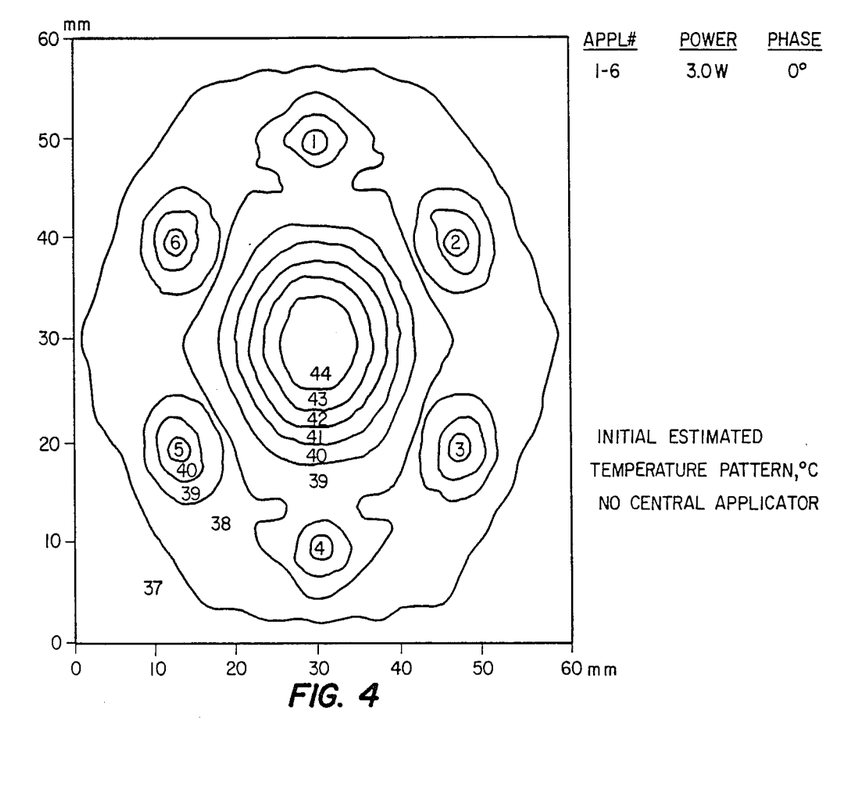
FIG. 4 is a view showing the computer estimated initial temperature pattern for the central plane of the six antenna array of FIG. 3 with no central antenna.

The input power and phase was set as shown in FIG. 4 for the phantom heating. This phase and amplitude was intended to be at 10 watts on each applicator and 0.0 phase but the system actually applied the power and phase shown. This was measured with other precision test equipment. The pattern of FIG. 4 is of the pretreatment planning prediction pattern without the centrally located probe being energized. The treatment planning predicts substantial central heating of a 14 mm wide zone at 42 degrees Celsius or more with much less heating near the array perimeter. The predicted temperature rise was 4.2 degrees Celsius for a one minute heating.

Figure 5A:
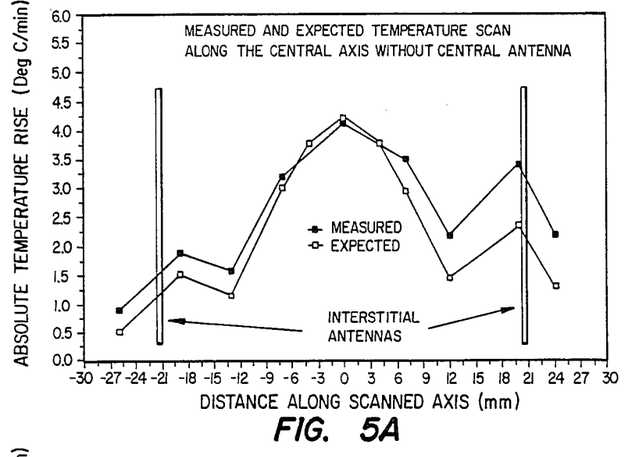
FIG. 5a is a view showing a plot of measured and expected temperature along the central axis of the apparatus of FIG. 3.

FIG. 5a shows a central axis plot comparing the measured data to the predicted plot. However, only predicted points were used for the plot where measurement catheters had been used. Thus, both have straight lines joining discrete points. Very good correlation is seen between these two curves. There is seen more heating near each applicator than predicted. This local antenna heating is normally moderated during treatments by blood flow and thermal conduction effects especially along the perimeter zone. So the predicted pattern may more accurately represent that expected near each applicator during clinical use. The pattern shows as predicted the highly heated central zone which was seen to rise 4.1 degrees Celsius per minute at the center. This agrees very well to the predicted rate of 4.2 degrees Celsius per minute.

Figure 5B:
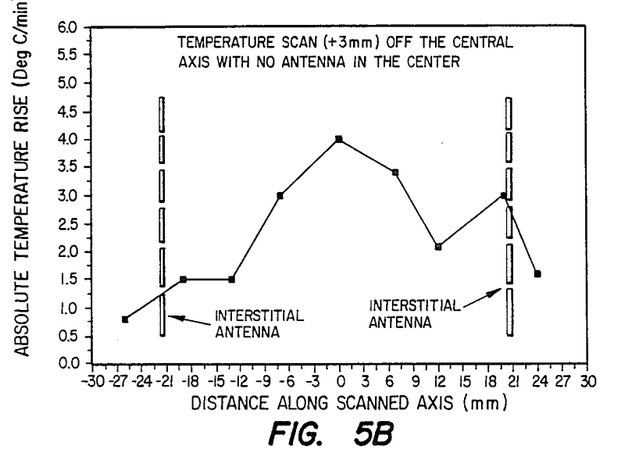
FIGS. 5b and 5c are views showing plots of measured temperatures at regular intervals off the central axis of the apparatus of FIG. 3.

FIG. 5b shows the measured temperatures along the 3 mm scan axis. This scan is very similar to the central axis but with reduced heating near the applicators. A rapid drop off is shown outside the array area as predicted.

Figure 5C:
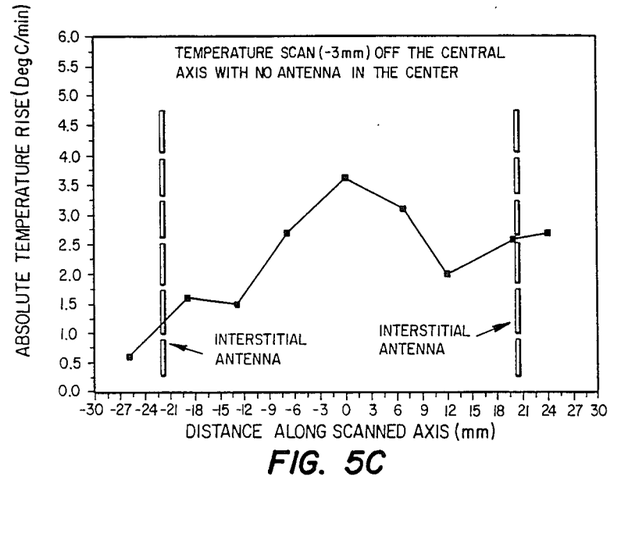

FIG. 5c is almost identical to FIG. 5b and shows a similar temperature pattern at the −3 mm axis. Each of these tests were separate heating tests with the same system power, phase, and heating times. Thus, repeatability is demonstrated and the pretreatment planning is verified to agree with actual measurements. The problems of the excessive central heating is clearly demonstrated.

The solution to the problem given by the present invention is to utilize a low power central antenna with a slight phase lead relative to the perimeter antennas. FIG. 6 and FIGS. 7a–7c demonstrates the success of the invention.

Figure 6:
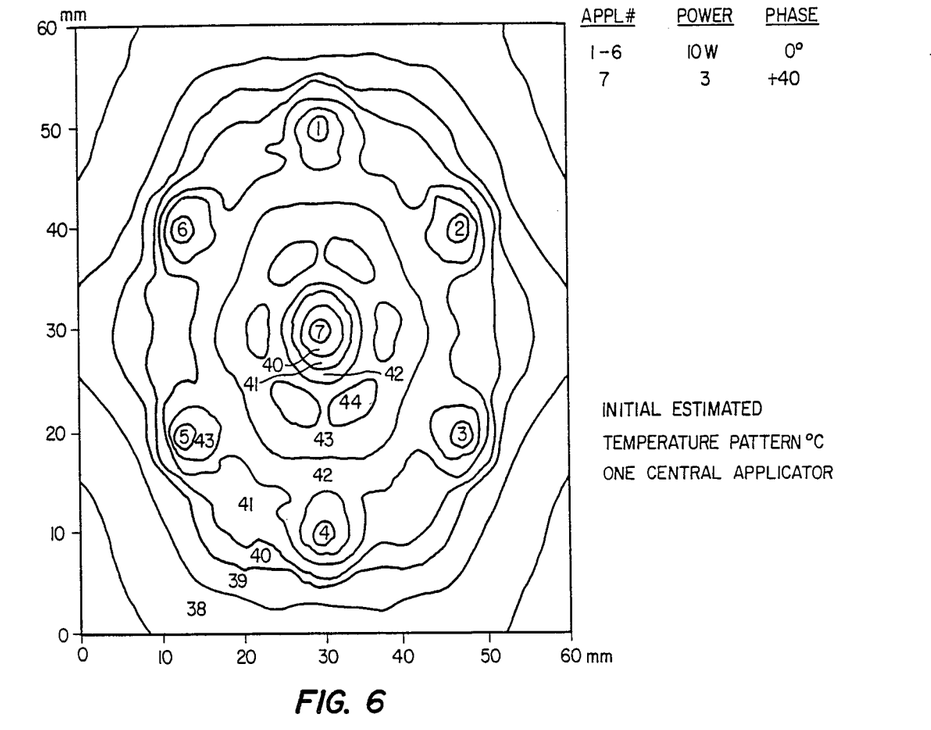
FIG. 6 is a view showing the computer estimated initial temperature pattern for the central plane of the apparatus of FIG. 3 with a central antenna.

Referring now to FIG. 6, FIG. 6 shows the pretreatment planning solution of the same basic array configuration of FIG. 4, but with the added 3 watt central antenna 48 shown as a circled 7 in the Figure. The power and phase shown is that measured by calibrated test equipment. The individual channel powers of the system were set to about 10 watts and equal phase except for the central antenna 48, which was set at 3 watts, and 18 degree lead. The phase lead was accomplished by simply inserting a piece of coax cable having a phase delay of 330 degrees. This in effect is the same as a 30 degree phase lead. It happened that the power channel used for the central applicator had a 12 degree lag. Thus, the resultant was the modeled 18 degree phase lead.

The power radiated from the antenna 48 in the center was approximately 198 degrees out of phase with the power arriving at this central zone by the perimeter antenna 46 shown by circled numbers 1–6. This caused a local partial cancellation of the central power and increased the heating of the outer margin of tissues as predicted. The predicted width of the effective heating zone is shown to be about 36 mm wide at 42 degrees Celsius or more for this 40 mm diameter array geometry. Without the central antenna the width was only 14 mm (FIG. 4).

Figure 7A:
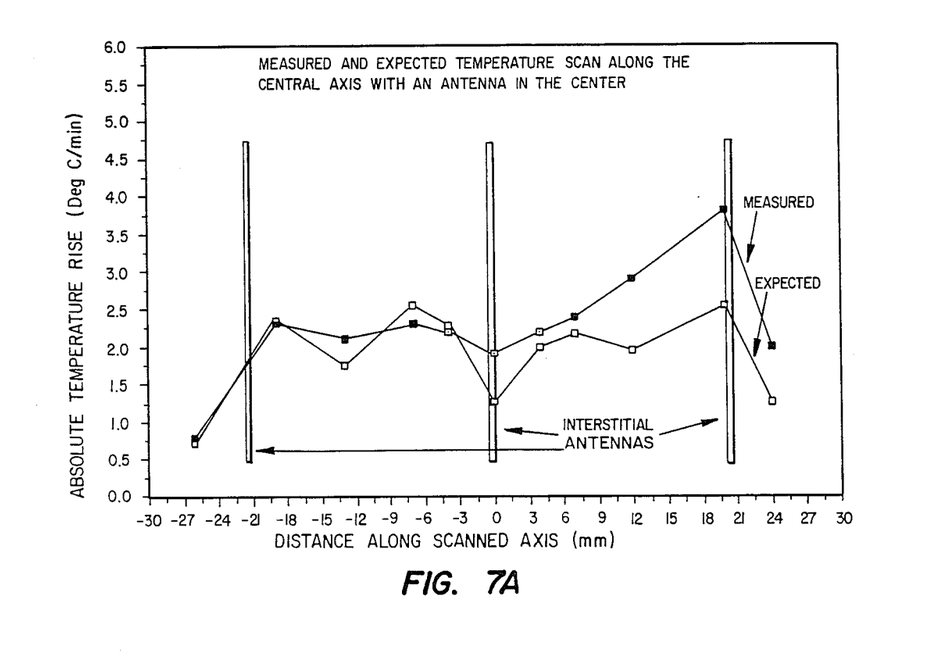
FIG. 7a is a view showing a plot of measured and expected temperature scan along the central axis of FIG. 3 with the central antenna.

FIG. 7a shows a comparison of the expected temperature rise from the treatment plan at the measurement points and the experimental measurements along the central axis. The measured temperature rise along the central axis is shown together with the expected. Again, the solid squares indicate the actual temperature measurement points. The central open square of the measured curve is that measured by inserting an accurate temperature probe (Bowman probe) before and after heating. The two other open squares are estimated points and were not actual measurements. The heat pattern, as predicted, has been flattened out where the central selective heating has been reduced. There does appear to be some additional heating on the right side. If the system used were, for example, the BSD-500, the system would automatically reduce power on applicator 4 to better smooth the temperature distribution once the target temperature is reached.

The measurements appear somewhat smoother than the expected from pretreatment planning which is expected since the heating experiment is for 60 seconds. This time allows a small degree of equalization between close hotter and cooler zones. It will be observed that both measured and expected show a slight central drop in temperature as a result of the inserted central antenna. It will be noted that this type of temperature distribution is much more uniform throughout the whole implant volume. This is much better for uniform heating of the whole tumor to be treated.

Figure 7B:
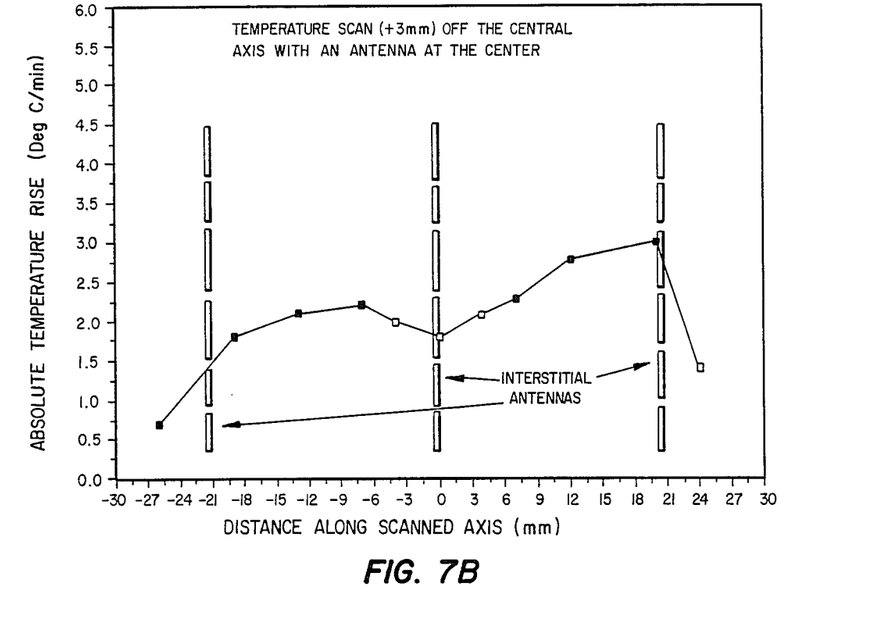
FIGS. 7b and 7c are views showing plots of measured temperatures at regular intervals off the central axis of the apparatus of FIG. 3 with the central antenna.

FIG. 7b shows the measured temperature rise in another 60 second heating along the +3 mm axis. The uniformity of the pattern is similar to the central axis, but the sensor very close to the antenna on the right is less as the temperature measurement is 3 mm away from the antenna as shown in FIG. 3. In this Figure the central point shown is not a measured point, but is estimated from the central axis measured data.

Figure 7C:
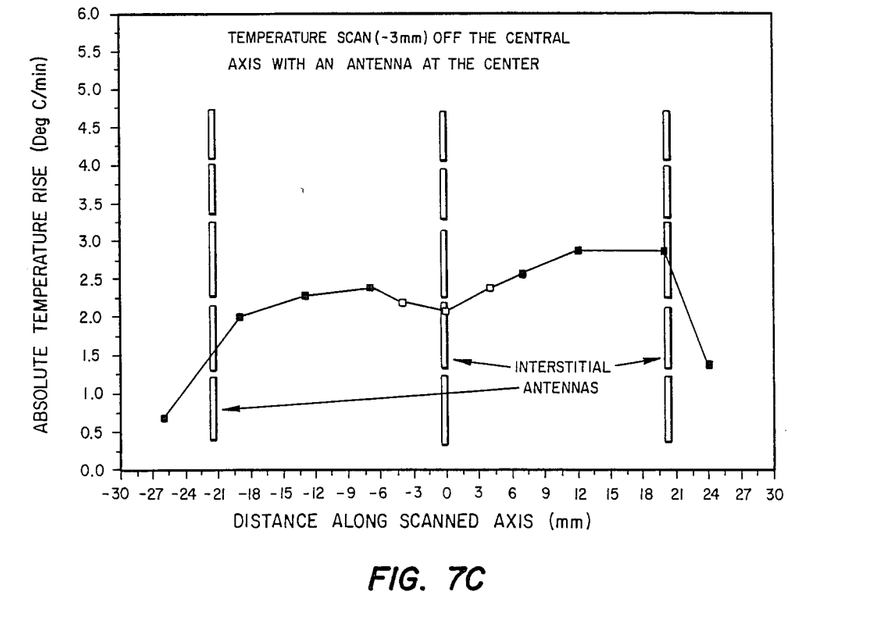

FIG. 7c shows a very similar measured pattern along the −3 mm measurement axis. This was again a repeated heating session, and the open central squares are not measured points but are estimated points.

Figure 8:
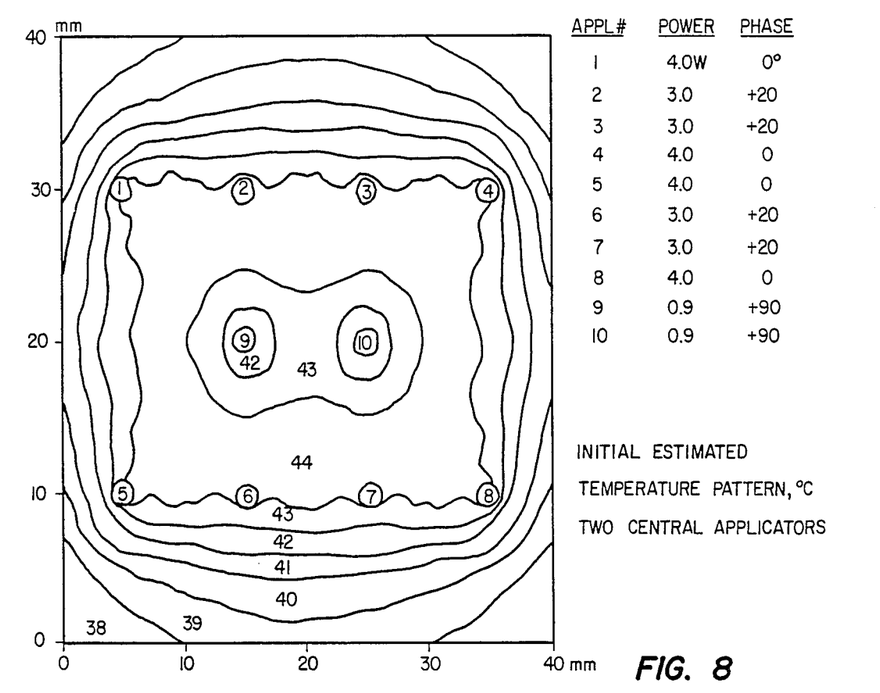
FIG. 8 shows the initial estimated temperature pattern along the central heating plane where two central applicators are placed in a large array to create a central partially destructive phase zone.

Referring now to FIG. 8, FIG. 8 shows the pretreatment planning solution of the initial estimated temperature pattern in degrees Celsius of a rectangular pattern having 8 peripheral and two centrally disposed applicators. Again, the principle of the invention is predicted to provide very wide spread heating within the implant zone even for rectangular implants and multiple central antennas.

Figure 9:
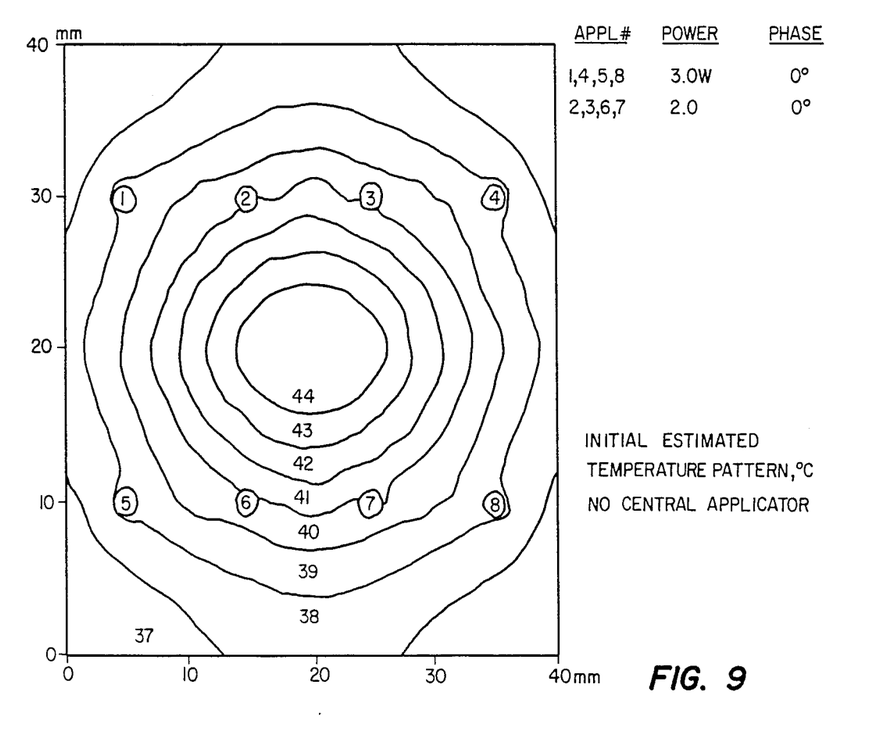
FIG. 9 shows the undesirable central hot spot predicted when the two central antennas are removed.

FIG. 9 shows the pretreatment planning pattern predicted by the computer solution if the two central antennas had not been included. Without the central applicators the heating width was much confined to only the central area.

The computer solution method includes the following steps:

1. Estimating the relative power phases for the applicators using the formula Pt=0.0894 DF.

2. Generating a look up table for Electric Field intensity, relative phase, and 3-D vector alignment within high water tissue at the operating frequency. This is done by careful measurements or by numerical modeling of the antenna applicator. The primary data needed is that along the central depth axis which is perpendicular to the applicator coaxial shaft.

3. Dividing the display area into sub-cells, for example squares, rectangles, or triangles.

4. Calculating the E-field potential for each corner point of the sub-cells in the array space using standard vector addition of fields as complex vectors.

The solution becomes quite simple along the central plane perpendicular to the applicators as the E-fields are all aligned with the applicator axis in this plane. Hence, the complex vector summation simply consists of accounting for the relative phase and E-field intensity for points in the central plane summing fields from each applicator as an amplitude and phase vector.

5. Once the sub-cell corner points in a display plane have been solved, estimating and plotting other points using bi-linear interpolation for the intensity zones to be displayed.

6. Repeating steps 2 through 5 for determining for each probe the power and phase distribution for each applicator to obtain a desired uniform heating pattern.

In this way initial operator estimates of phase power settings can be chosen and the resulting heat field estimated. Repetition of this procedure enable optimization of the power and phase settings for various interstitial microwave arrays.

Although several embodiments of the invention have been described, it will be apparent to a person skilled in the art that various modifications or details of construction shown and described may be made without departing form the scope of the invention.

What is claimed is:

1. An electromagnetic hyperthermia system for heating local regions within living body tissue comprising:
    (a) a microwave generator for producing microwave energy at a preselected frequency;
    (b) a power dividing means operatively connected to the microwave generator for dividing the microwave energy selectively for distribution;
    (c) applicator means operatively connected to the power dividing means for radiating the microwave energy into surrounding body tissue, the applicator means including a plurality of applicator groups and at least one applicator for central location within the plurality of applicator groups to thereby define an array when geometrically arranged about a selected area of living body tissue; and
    (d) a phase and power microwave energy control means including a plurality of preselected phase and power setting means connected to the plurality of applicator groups and to the at least one applicator for central location for supplying power in phase to the plurality of applicators and for providing the at least one central applicator with power and phase selection sufficient to cause a partial destructive interference zone in a central zone of the array, and means responsive to a reference temperature signal and signals of the temperature sensor means for producing microwave energy control signals for adjusting the amount of radiated microwave energy to each applicator whereby the distributed microwave energy is radiated sufficiently to treat the tissue area with a predetermined heating pattern for destroying cancerous growth within the array while leaving unharmed the normal tissue surrounding the applicator array.

2. An electromagnetic hyperthermia system according to claim 1 wherein the microwave energy control means further includes a plurality of microwave energy regulators taken from the group consisting of attenuators, switches, adjustable gain amplifiers, and mismatched tuning sections.

3. An electromagnetic hyperthermia system according to claim 1 wherein the microwave energy control means includes either electronic or mechanical phase shifters.

4. An electromagnetic hyperthermia system according to claim 1 wherein phase means of the phase and power means includes a plurality of phase adjustment devices having a plurality of microwave energy phase shifters from the group consisting of phase delay coaxial cables, phase shift modules, and ferrite phase shifters.

5. A method for operating a hyperthermia electromagnetic radiation applicator system including a multiplexer, a plurality of applicators, a temperature signal sensing device for indicating temperature variations in surrounding body tissue, and a control means, said method comprising the steps of:
    (a) providing microwave energy from microwave energy sources through the multiplexer to the plurality of applicators;
    (b) selecting a phase shift of one or more central applicators of the applicator array to partially reduce the central power by a partial destructive interference zone to increase peripheral heating;
    (c) estimating signals indicative of temperature variations from the temperature signal sensing device, comparing the signals indicative of the estimated temperature to signals of a desired temperature pattern for determining microwave energy correcting signals; and
    (d) correcting the microwave energy input to the applicators using said correcting signals for obtaining a desired heat pattern.

6. A method of adjusting an array of microwave applicators for hyperthermia treatment and display using partial coherent phase microwave energy destruction comprising the steps of:
    (a) generating a look up table for electric field intensity, relative phase, and 3-D vector alignment within high water content living tissue at a selected operating frequency;
    (b) dividing an area representative of said living tissue for display into an array of sub-cells having preselected geometrical shapes with an applicator at the corner point of such sub-cells;
    (c) calculating for each corner point of the array with a center of sub-cells in a display plane an electric field potential using vector addition of fields as complex vectors using relative phase and electric field intensity values for points in the vector summing fields from each applicator as selected from the look up table;

(d) estimating electric field potentials of additional points within the plane using bi-linear interpolation; and (e) repeating steps a through d for determining for each applicator the power and phase distribution for each applicator of a peripheral array of applicators and at least one centrally located applicator for destructive partial cancellation of the microwave energy at the center of the array necessary for obtaining a desired uniform heating pattern.

7. A method according to claim 6 further including the step of estimating the relative electric field potential values for points in a display plane for reducing the number of iterations required in determining the values for producing a desired uniform heating pattern.

* * * * *